United States Patent [19]
Hart et al.

[11] Patent Number: 5,334,198
[45] Date of Patent: Aug. 2, 1994

[54] SURGICAL INSTRUMENT

[75] Inventors: Rickey D. Hart, North Attleboro, Mass.; Richard M. Winters, Cary, N.C.; John T. Rice; James E. Nicholson, both of Lincoln, Mass.

[73] Assignee: Innovasive Devices, Inc., Hopkinton, Mass.

[21] Appl. No.: 959,121

[22] Filed: Oct. 9, 1992

[51] Int. Cl.$^5$ .................................. A61B 17/40
[52] U.S. Cl. .................................. 606/52; 606/49
[58] Field of Search .............. 606/32, 39, 41, 45, 606/46, 51, 52, 170, 205–209

[56] References Cited

U.S. PATENT DOCUMENTS

| | | | |
|---|---|---|---|
| 1,813,902 | 7/1931 | Bovie | 606/52 |
| 2,113,246 | 4/1938 | Wappler | 606/205 |
| 3,404,677 | 10/1968 | Springer | |
| 3,763,860 | 10/1973 | Clarke | 128/340 |
| 3,938,527 | 2/1976 | Rioux et al. | 606/51 |
| 4,003,380 | 1/1977 | Wien | 606/51 |
| 4,005,714 | 2/1977 | Hiltebrandt | 606/51 |
| 4,018,228 | 4/1977 | Goosen | 128/2 |
| 4,054,143 | 10/1977 | Bauer | 606/52 |
| 4,174,715 | 11/1979 | Hasson | 128/321 |
| 4,232,676 | 11/1980 | Herczog | 128/303.14 |
| 4,271,838 | 6/1981 | Lasner et al. | 128/318 |
| 4,370,980 | 2/1983 | Lottick | 128/303.17 |
| 4,393,872 | 7/1983 | Reznik et al. | 604/151 |
| 4,669,470 | 6/1987 | Brandfield | 128/318 |
| 4,674,499 | 6/1987 | Pao | 128/303 |
| 4,674,501 | 6/1987 | Greenberg | 128/305 |
| 4,686,980 | 8/1987 | Williams et al. | 128/303.13 |
| 4,763,668 | 8/1988 | Macek et al. | 128/751 |
| 4,872,456 | 10/1989 | Hasson | 128/321 |
| 4,949,717 | 8/1990 | Shaw | 606/147 |
| 5,026,370 | 6/1991 | Lottick | 606/42 |
| 5,089,007 | 2/1992 | Kirsch et al. | 606/205 |

*Primary Examiner*—Stephen C. Pellegrino
*Assistant Examiner*—M. Peffley
*Attorney, Agent, or Firm*—Pandiscio & Pandiscio

[57] ABSTRACT

An improved surgical tool of the type comprising a handle assembly having a movable tool-operating handle member, a tool head having first and second tissue-engaging members movable between open and closed positions relative to one another, and a mechanism coupling the tool head to the handle assembly for causing opening and closing movement of the tissue-engaging members in response to manipulation of the movable tool-operating handle member. The improved tool is characterized by an inner shaft secured to a stationary part of the handle assembly, and a hollow outer shaft disposed in telescoping relation to the inner shaft, with the tool head being secured to the inner shaft and the outer shaft being movable axially relative to the inner shaft by manipulation of the movable tool-operating handle member, with the outer shaft causing opening and closing of the tissue-engaging members as it undergoes telescoping movement. Preferably an opaque tubular member surrounds the hollow outer shaft so as to conceal movement of the outer shaft. The tool also may include a manually-operated mechanism for selectively rotating the tool head relative to the handle assembly.

43 Claims, 10 Drawing Sheets

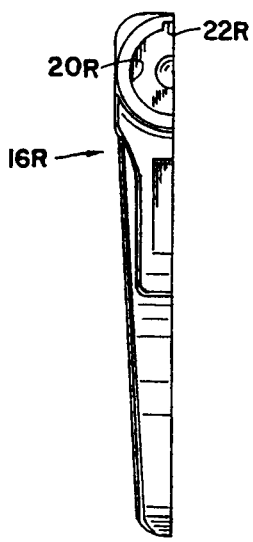
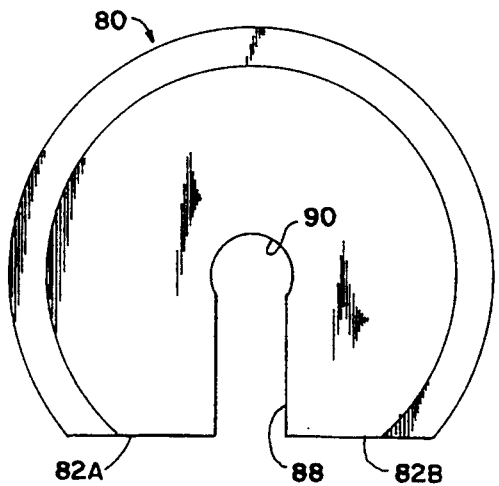
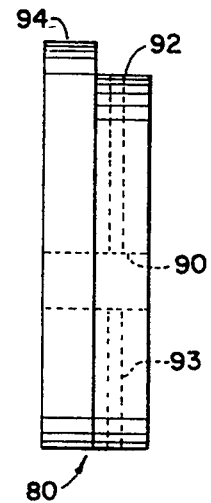
FIG. 4          FIG. 8          FIG. 9
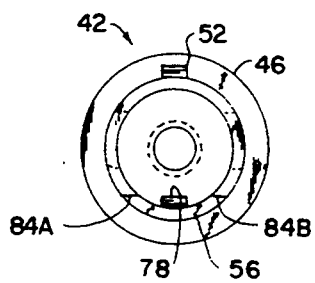
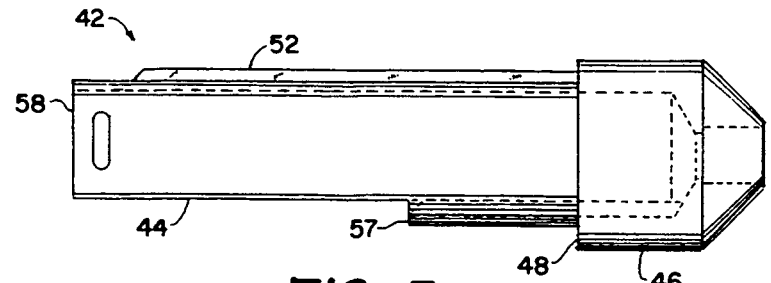
FIG. 7          FIG. 5
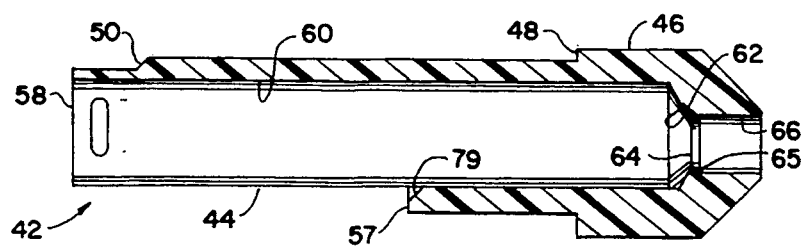
FIG. 6

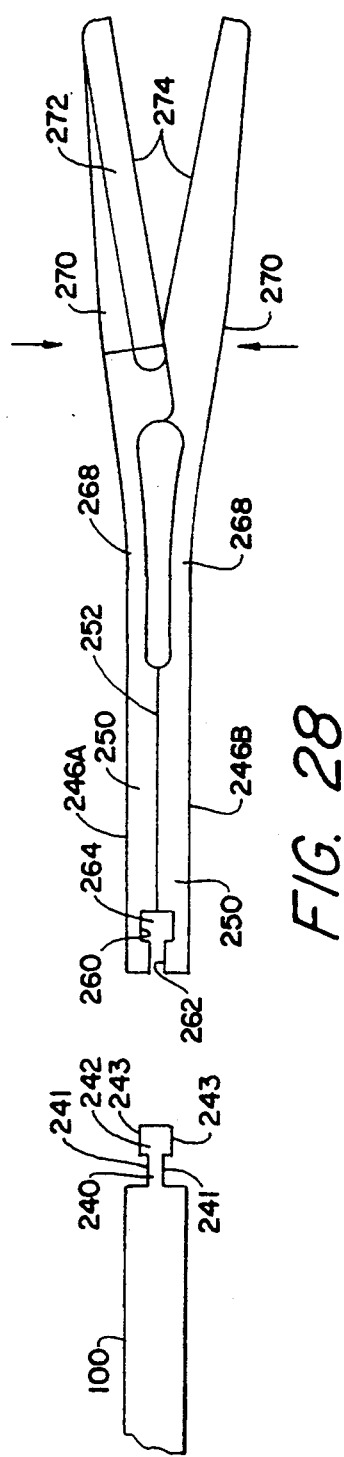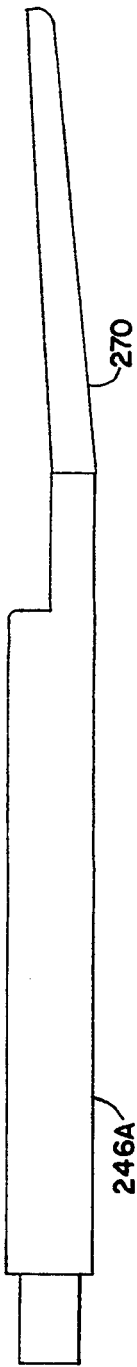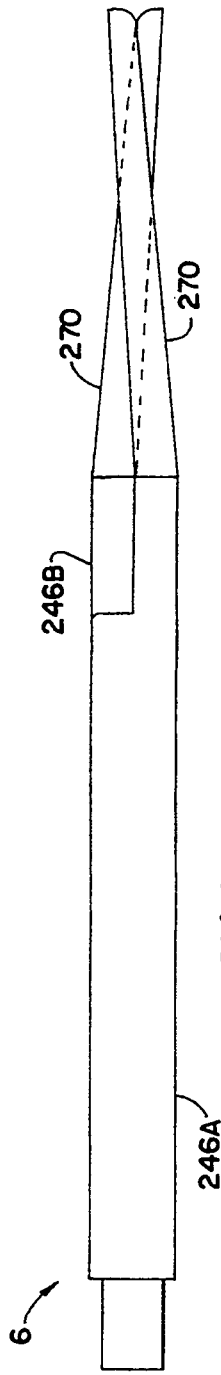

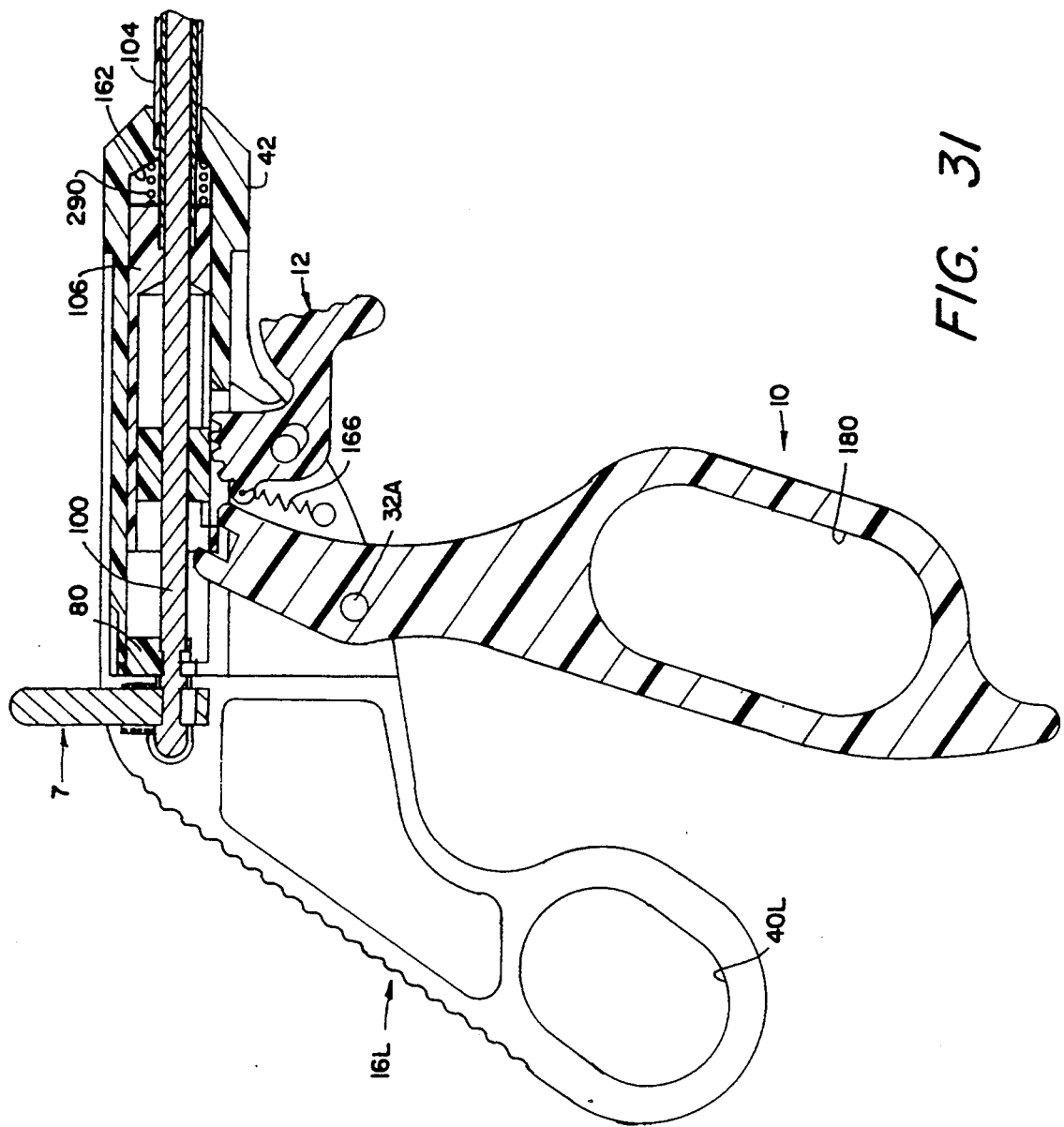

SURGICAL INSTRUMENT

INTRODUCTION

This invention relates to surgical instruments and more particularly to instruments for use in endoscopic surgical procedures, including but not limited to laparoscopy.

BACKGROUND OF THE INVENTION

Human and animal surgery frequently requires the grasping, manipulating or cutting of tissue or other organic living matter at some distance from the surgeon's hands. In such cases endoscopic surgical methods are commonly employed that make it possible for skillful and precise surgery to be conducted despite the fact that the surgical site is a substantial number of inches from the point of initial incision in the person or animal being operated on. Endoscopic surgical procedures encompass both arthroscopic and laparoscopic surgery techniques. In endoscopic surgery, small incisions are made in the exterior surface of the person or animal being operated on, and the work being performed is observed by the operating surgeon by means of a an optical device known as an endoscope which is inserted into the person or animal through a small incision. Endoscopic surgical techniques are displacing conventional open surgical techniques for many procedures, and hence there is a need for improved instruments for conducting such procedures.

A wide variety of surgical instruments have been devised for use in arthroscopic and laparoscopic surgical procedures, including instruments such as graspers, forceps and scissors for use in grasping, cutting or otherwise remotely manipulating bodily tissue and other matter during surgery.

A typical instrument employed in endoscopic surgery has a pair of articulated jaws, and a handle mechanism comprising two members, one movable with respect to the other, which can conveniently be manipulated so as to cause the jaws to open and close. Serrations, blades, cutting edges, or other features (depending upon the use for which the tool is intended) enable the jaws to perform various surgical functions, such as grasping or cutting. The articulated jaws are located at the distal end of a relatively long extension of the handle mechanism. The length of the extension is determined by the depth of the surgical site, while its cross-sectional dimensions are established by the maximum permissible incision size.

Many ingenious linkages have been devised for converting the surgeon's manual efforts at the handle end of the instrument into opening and closing of the tool's jaws. Most commonly, the surgical tool comprises a stationary handle member rigidly joined to a hollow outer shaft and a movable handle member pivotally attached to a coaxial inner shaft in the form of a tube or solid rod that is capable of reciprocal axial movement relative to the outer shaft, with the jaws being operatively coupled between the outer hollow shaft and the inner shaft member so as to open and close in accordance with relative axial movement of the outer and inner shafts. When the surgeon squeezes the stationary and movable handle members together, the outer and inner shafts coact in such a way as to make the jaws close. When the surgeon spreads the stationary and movable handle members apart, the motions are reversed and the jaws open. Publications illustrating the prior art include U.S. Pat. No. 3,404,677 and the prior art cited therein, as well as the following references: U.S. Pat. Nos. 4,836,205; 4,258,716; 4,084,594; 4,393,872; 5,026,375; 4,712,545; and 5,026,370.

OBJECTS AND SUMMARY OF INVENTION

A factor involved in the development of this invention is the realization that in the case of surgical scissors involving two telescoping shafts, having the outer hollow shaft fixed to the stationary handle member, in preference to it being movable and the inner shaft being fixed relative to the stationary handle member, is beneficial in that it avoids the possibility that apparent movement of the outer shaft when the instrument is operated would confuse the surgeon's depth perception in relation to the surgical site of the patient, thereby increasing the likelihood of surgical error.

Still other factors involved in development of this invention are the advantages derived from designing a surgical instrument with discrete subassemblies so as to facilitate (1) manufacture, (2) use of replaceable components, and (3) sterilization of selected components or subassemblies. Another factor considered in making the invention is the desirability of an instrument design that optionally includes a cauterization capability.

Accordingly, the primary object of this invention is to provide an improved surgical tool for use in endoscopic surgical procedures, e.g., laparoscopic surgery.

Another object of this invention is to provide an improved surgical instrument of the type described that is formed of a plurality of discrete subassemblies that facilitate manufacture and final assembly.

Still another object of this invention is to provide a surgical tool having a novel handle assembly.

A further object of this invention is to provide a surgical instrument or tool that comprises a tool head and means for electrifying said tool head so as to effect cauterization of tissue contacted by said tool head.

Still a further object is to provide a precision surgical instrument of the type described that is characterized by a removable scissors-type cutting head.

Another object of this invention is to provide a surgical instrument adapted for cutting tissue that does not confuse the surgeon into believing that the instrument is moving axially when it is operated without any intention on his part to move it axially.

A further object of this invention is to provide an improved surgical instrument of the type that has (1) a handle assembly and (2) a tool head coupled to and operated by the handle assembly that comprises co-operating jaws movable into and out of closing relation with one another, wherein the jaws are coupled to and operated by a coaxial arrangement of a rod secured to the handle assembly and a hollow shaft slidably surrounding the rod, the improved surgical instrument being characterized means for concealing axial movement of the tube relative to the handle assembly.

A further specific object of this invention is to provide a surgical instrument characterized by a movable tube and a sheath that conceals axial movement of that tube.

Another specific object of the invention is to provide a surgical tool for use in various surgical procedures, including but not limited to endoscopic procedures for arthroscopy and laparoscopy, that comprises a handle and trigger assembly separably connected to an operating tool assembly that in turn comprises a hollow shaft and a rod telescopically mounted to one another, means for securing the rod to the handle assembly, and means connecting the hollow shaft to the trigger assembly whereby operation of the trigger will cause the shaft to move axially relative to the rod.

Another specific object of this invention is to provide a novel surgical instrument that is adapted for monopolar electrification, so as to permit cauterization at the surgical site.

The foregoing objects are obtained by providing a surgical instrument or tool that comprises a handle assembly having first and second handle members movably connected for movement relative to one another, an elongate rod releasably secured to the first handle member so as to form a fixed extension thereof, a tool head coupled to the rod having first and second members movable toward and away from one another, a tube (hollow shaft) coaxially and slidably surrounding the rod, with the tube having a first end slidably received in the handle assembly and a second end in position to be moved into and out of overlapping relation with said first and second members of said tool head, and drive means connecting said hollow tube and one of said handle members for causing said tube to shift axially relative to said rod between (1) a first retracted position when said one handle member is moved to a first position relative to the other handle member and (2) a second extended position when said one handle member is moved to a second position relative to said other handle member, said first and second members of said tool head being in a first open position relative to one another when said one handle member is in its said second position and being forced by said tube to close relative to one another when said one handle member is moved to its said first position. In a preferred embodiment of the invention, (1) the tool head is detachable from the aforementioned rod and replaceable by another like or different tool head; (2) the tool head is rotatable relative to the handle assembly; (3) the rod, tool head and hollow tube form a subassembly that is readily detachable from the handle assembly; and (4) the tool head may be electrified for monopolar cauterization.

Other necessary and optional features are disclosed by or rendered obvious by the following detailed description which is to be considered together with the accompanying drawings.

THE DRAWINGS

FIG. 4 is a front view in elevation of the handle part shown in FIG. 3;

FIG. 5 is a side elevation of the insulator housing;

FIG. 6 is a sectional view in side elevation of the insulator housing taken along its center line;

FIG. 7 is a rear end view of the insulator housing;

FIG. 8 is a front end view in elevation of a cap for the insulator housing;

FIG. 9 is a side view in elevation of the end cap of FIG. 8;

FIG. 28 is an exploded view showing how the tool head is detachable from its supporting rod;

FIG. 29 is a top plan view of one of the scissors blade members;

FIG. 30 is a top plan view of the tool (scissors) head in open position; and

FIG. 31 is a fragmentary sectional view showing inclusion of a spring for holding the trigger member in its forward position.

It is to be understood that some of the several views presented by the drawings are drawn to different scales for ease of illustration and description. Also, like parts and features are identified by like numerals in the drawings.

PREFERRED EMBODIMENT OF INVENTION

Figure 1:
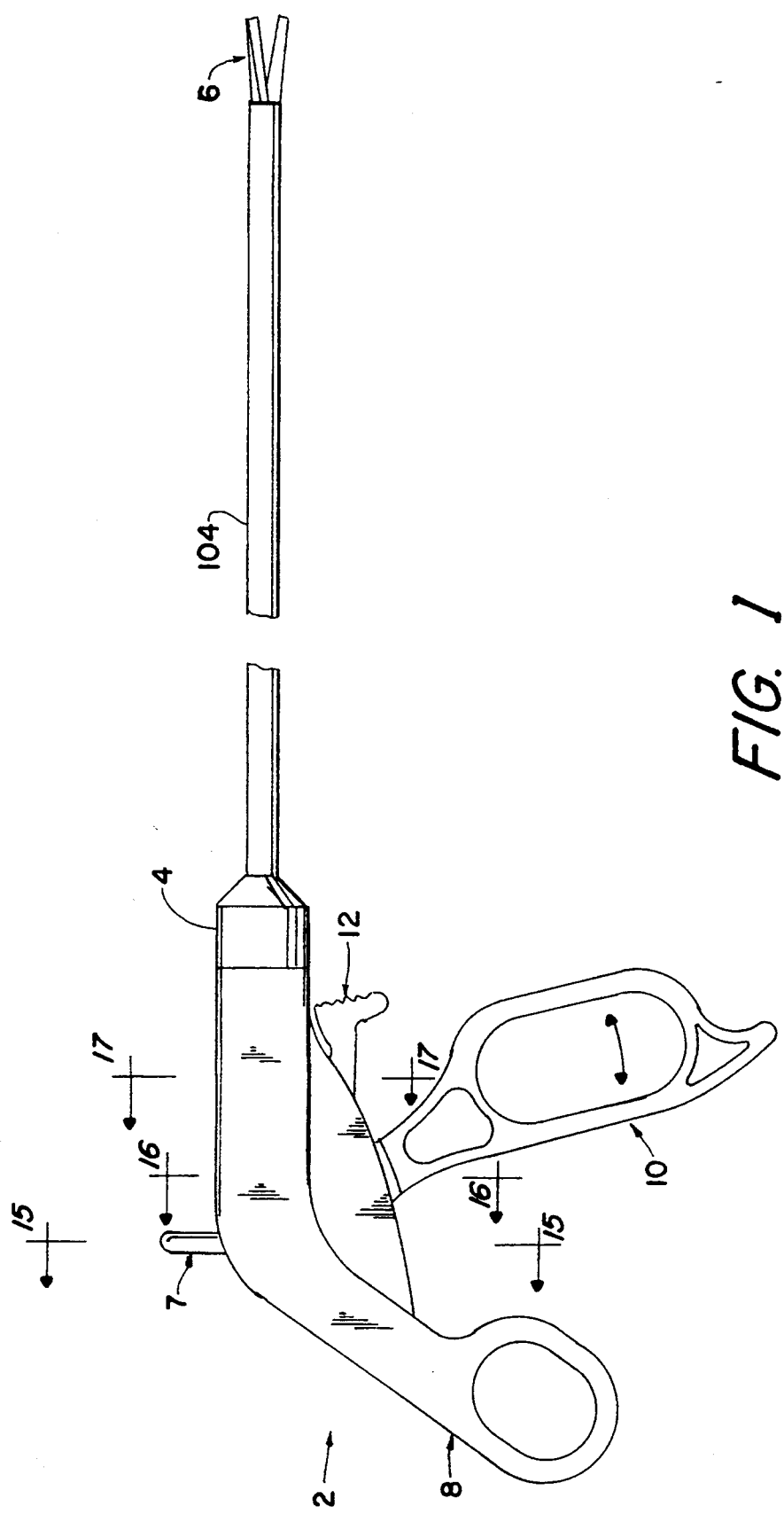
FIG. 1 is a side elevation of a preferred embodiment of the invention constituting a surgical scissors designed for laparoscopic surgery.

Referring now to FIG. 1, there is shown a surgical instrument which, in its preferred form, is a scissors designed for laparoscopic procedures. The instrument comprises a handle assembly 2, a drive assembly 4, a tool head 6 in the form of a scissors head, and an electrical terminal pin 7. The handle assembly may take various forms. In this preferred embodiment of the invention, the handle assembly comprises a fixed or stationary handle 8, a movable handle member in the form of a trigger 10 for operating the scissors head, and a rotation trigger member 12 which cooperates with the drive means carried by the handle assembly to effect controlled rotation of the scissors head relative to the handle assembly.

Figure 2:
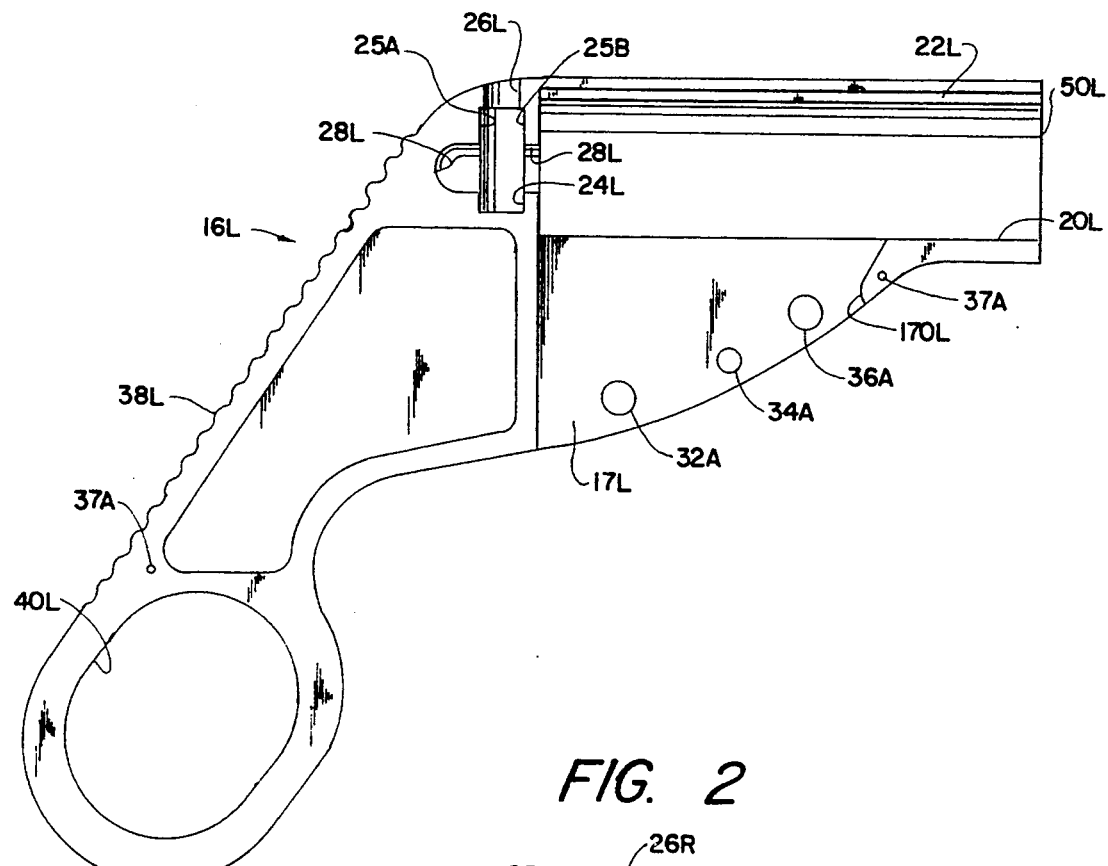
FIG. 2 is a side view in elevation of the left hand half of the handle housing.
Figure 3:
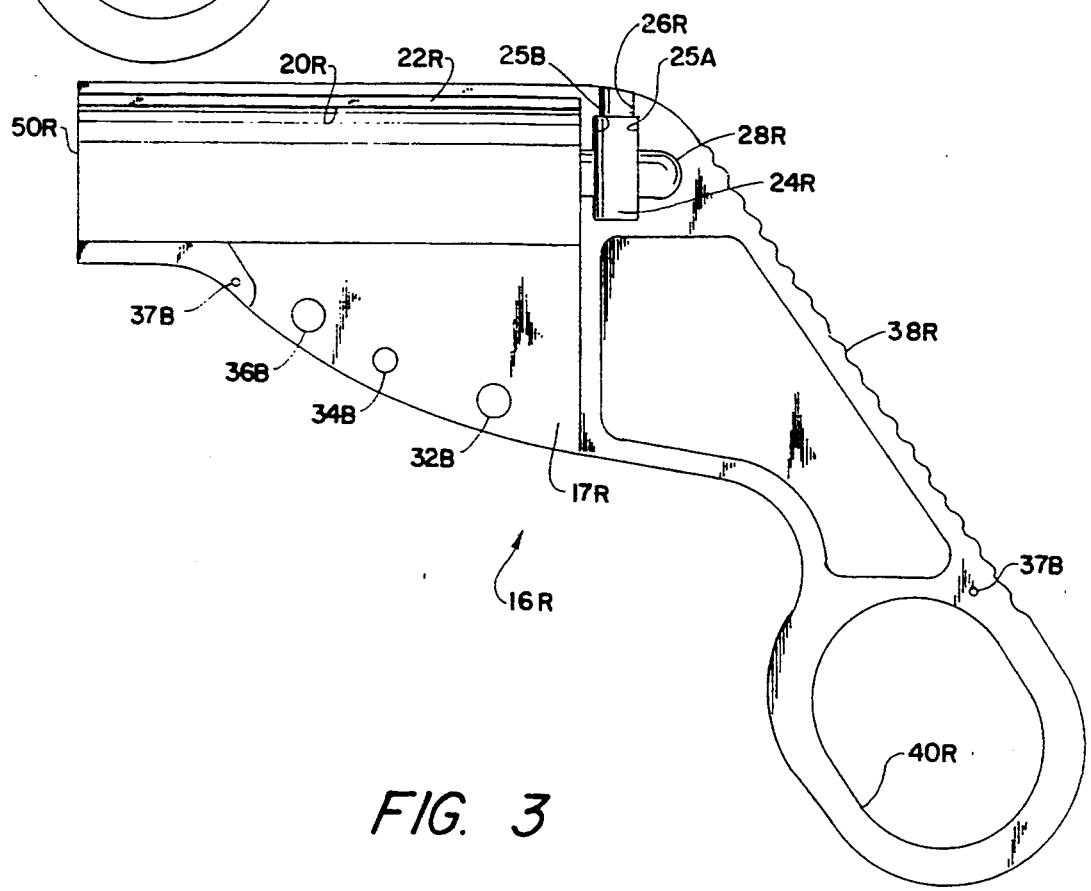
FIG. 3 is a side view in elevation of the right hand half of the handle housing.

Looking now at FIGS. 2-4, the fixed handle 8 comprises complementary left-hand and right-hand handpieces 16L and 16R that preferably are made of a plastic material such as a polysulfone or polycarbonate. These handpieces are complementary in the sense that they are mating halves of member 8 and, except as otherwise stated hereinafter, handpieces 16L and 16R are identical mirror images of one another. Handpieces 16L and 16R have like circularly curved axially-extending elongate cavities 20L and 20R respectively on their mutually confronting sides. Additionally, handpieces 16L and 16R have axially-extending flat-sided grooves 22L and 22R that intersect cavities 20L and 20R respectively at the twelve o'clock position (FIG. 4). Grooves 22L and 22R cooperate to define a keyway for an insulator housing 42 (FIGS. 5-7) described hereinafter that forms part of the drive assembly 4. Handpieces 16L and 16R also have semi-circular cavities 24L and 24R that communicate with reduced-diameter semi-circular cavities 26L and 26R respectively. Intersecting the cavities 24L and 24R are additional semi-circular cavities 28L and 28R which also intersect the cavities 20L and 20R respectively at right angles. Cavities 20L, 20R, 24L, 24R, 26L, 26R, 28L and 28R are semi-circular in the sense that they have a semi-cylindrical cross-section. The left handpiece 16L is provided with three projections or pins 32A, 34A and 36A of circular cross-section that are sized to make a close fit in like-spaced cavities or depressions 32B, 34B and 36B in the right handpiece 16R. Although provided for other purposes hereinafter described, pins 32A, 34A and 36A serve incidentally as assembly registration pins for handpieces 16L and 16R.

Preferably, but not necessarily, one handpiece (16L) has two or more locating pins 37A that are sized and located so as to mate closely with shallow depressions or cavities 37B in the other handpiece (16R), so as to facilitate and assure proper registration of the two handpieces when they are engaged with one another in forming handle 8. Handpieces 16L and 16R are secured together, preferably by a suitable cement such as an epoxy resin or by ultrasonic welding.

For reasons of convenience of use by the surgeon, it is preferred, but not essential, that the rear surface of the left and right handpieces have a knurled configuration as shown at 38L and 38R respectively so as to facilitate gripping of the handle unit. Additionally, it is preferred, but not essential, that the handpieces be provided with complementary finger holes 40L and 40R for receiving the thumb of the surgeon.

Drive assembly 4 comprises an insulator housing 42 and a tube housing 106 (see FIG. 10 and FIGS. 5-7 and 18-21), plus components (other than tool head 6) that are attached to housings 42 and 106.

Cavities 20L and 20R in the two handpieces cooperate to form a cylindrical chamber for receiving insulator housing 42. The latter, which preferably is made of the same material as handpieces 16, comprises a cylindrically shaped elongate section 44 having a peripheral flange 46 at its forward or distal end so as to provide a shoulder 48 that engages the forward end surfaces 50L and 50R of the left and right handpieces. Tubular section 44 is formed with an external longitudinally-extending rectangular rib 52 at the twelve o'clock position (as viewed in FIG. 7) that is sized to make a close sliding fit in the keyway formed by grooves 22L and 22R of the left and right handpieces 16L and 16R respectively. In addition, tubular section 44 has an axially-extending slot 56 (FIG. 7) formed symmetrically about the six o'clock position (as viewed in FIG. 7) that serves as an access hole for portions of trigger members 10 and 12 and a slide hole for a portion of tube housing 106. As viewed in FIG. 7, slot 56 terminates in side edge surfaces 84A and 84B. The circumference of section 44 in the portion having slot 56, i.e., the circumference measured between the outer edges of side edge surfaces 84A and 84B, measures about 260°, so that slot 56 extends through an angle of about 100° (50° on either side of the six o'clock position). As viewed in FIGS. 5-7, slot 56 starts at the proximal (rear) end of section 44 and ends close to the midpoint of housing 42, leaving an arcuate end surface or shoulder 57 (FIG. 6).

Insulator housing 42 has a center bore 60 which is of constant diameter throughout its length, except that (1) at its distal (front) end it is tapered as shown at 62 and then communicates in turn with a smaller diameter hole 64 and a bore 66 that has a slightly larger diameter than hole 64 so as to form an annular shoulder 65, and (2) it is formed with an internal rectangular axially-extending rib 78 at the six o'clock position (as seen in FIG. 7). Preferably the proximal (rear) end of rib 78 is bevelled as shown at 79. Affixed to the proximal (rear) end of the insulator housing 42 is an end cap 80 (FIGS. 8 and 9) that preferably is made of the same material as handpieces 16. End cap 80 is generally circular in cross-section except that its circumference is less than a full 360°, so as to provide flat bottom surfaces 82A and 82B. Preferably its circumference, measured between the outer edges of surfaces 82A and 82B (as viewed in FIG. 8) measures about 240°. Consequently when cap 80 is applied to housing 42 so that its surfaces 82A and 82B extend parallel to bottom edge surfaces 84A and 84B, a portion of the rear end surface 58 of housing 42 in the region of the six o'clock position is not covered by cap 80, so as to allow clearance between the cap and trigger 10 when it is desired to pull the drive assembly out of the handle assembly.

Cap 80 is provided with a radially-extending through slot 88 that terminates at the center of the cap with a circularly curved hole 90 that is concentric with the center axis of the cap. Also cap 80 comprises a reduced diameter body section 92 and a peripheral flange 94. Body section 92 is sized to make a close fit in the proximal end of the insulator housing, with flange 94 having the same o.d. as tubular section 44. The cap is ultrasonically welded or cemented, e.g., by an epoxy resin, to the proximal end surface 58 of housing 42, with the circularly curved hole 90 being concentric with the hole 64 of housing 42.

Figure 10:
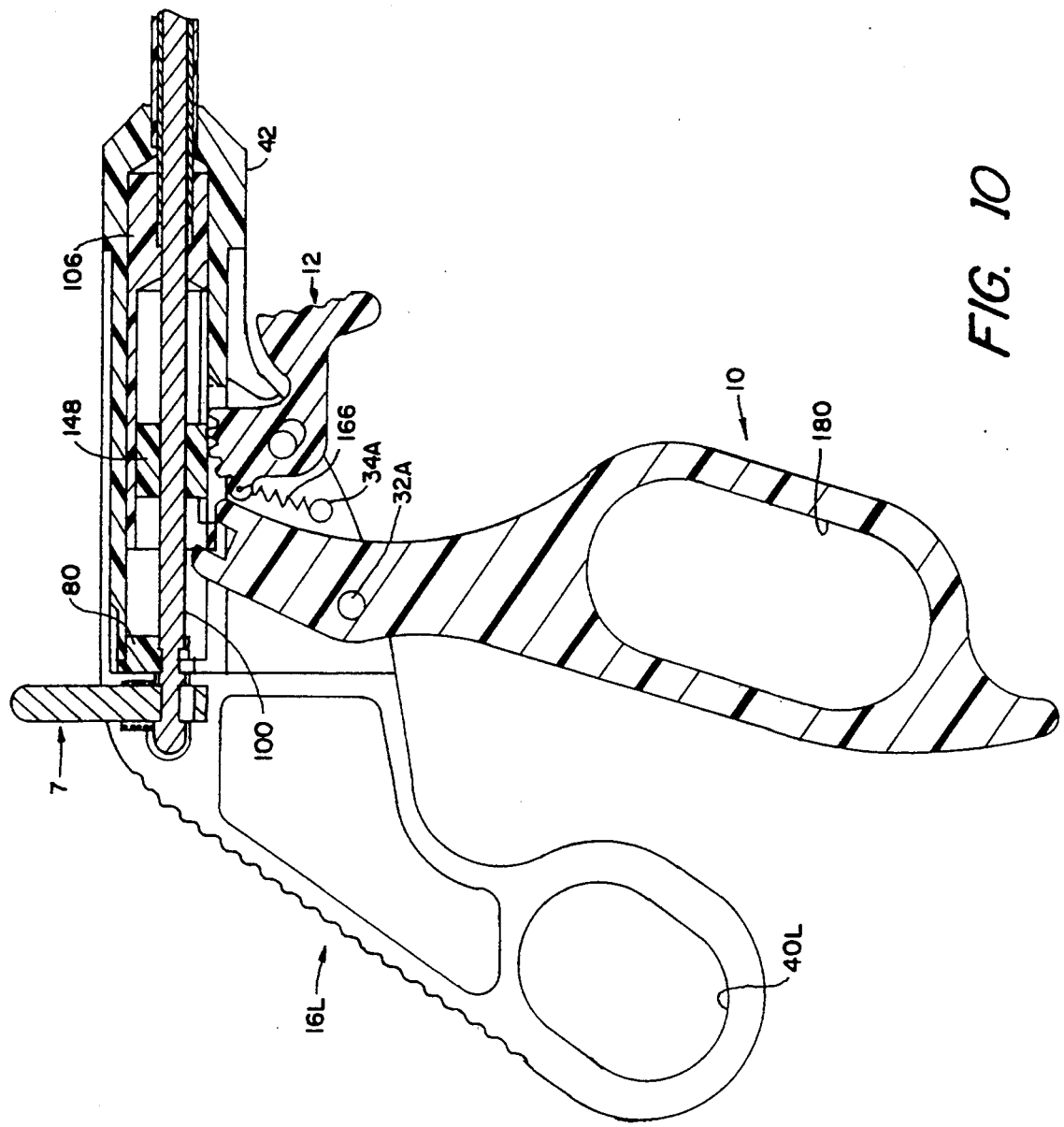
FIG. 10 is a fragmentary longitudinal sectional view in side elevation showing the handle assembly without the right hand half of the handle housing.

As shown in FIG. 10, insulator housing 42 is disposed in the cylindrical chamber formed by the mating cavities 20L and 20R of handpieces 16, with shoulder 48 engaging the forward end surfaces 50L and 50R of those handpieces and rib 52 being disposed in the keyway formed by grooves 22L and 22R. The interlocking of rib 52 with the keyway formed by grooves 22L and 22R serves to dictate orientation of housing 42 relative to the handle assembly. Housing 42 is releasably secured in handle assembly 2 by a locking action between a terminal pin 7 and rod 100 as hereinafter described.

Referring now to FIGS. 10-14 and 18-27, drive assembly 4 comprises, in addition to insulator housing 42, the following elements: a support rod 100 for tool head 6, an outer operating tube or sleeve 102, an outer sheath in the form of a tube 104, and a tube housing 106. The outer sheath 104 is cylindrical and its proximal (rear) end extends into axial bore 66 in engagement with shoulder 65 and is fixed to the insulator housing by a press fit or in some other suitable way, e.g., by an epoxy cement, as permitted by the materials being secured together. In this preferred embodiment, sheath 104 is made of a suitable electrically insulating material, e.g., a fluorinated hydrocarbon such as Teflon, while tube 102 may be made of an electrically-conductive metal or a conductive plastic. Tube 102 has an outer diameter sized so that it makes a close sliding fit within outer sheath 104 and also in the reduced diameter hole 64.

Figure 19:
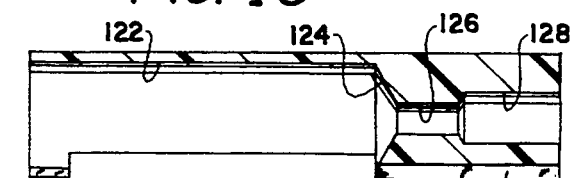
FIG. 19 is a longitudinal sectional view in elevation of the tube housing.
Figure 20:
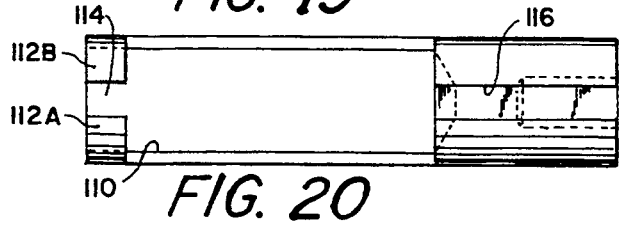
FIG. 20 is a bottom plan view of the tube housing.

Referring now to FIGS. 18–21, tube housing 106 preferably is made of a lubricious plastic material, e.g., molded DELRIN. Housing 106 is a hollow member formed with a rectangular aperture 110 that is centered about the six o'clock position and extends through about 100° of its circumference. Aperture 110 is located just short of the proximal or rear end of the tube housing, so as to form a depending lug section 112 which serves as part of the pivotal connection for the trigger member 10. Housing 106 also is provided with an axially-extending slot 114 that intersects aperture 110 and splits the lug section 112 into two like parts 112A and 112B (FIG. 20). Additionally, housing 106 has an external axially-extending shallow groove 116 located at approximately the six o'clock position. Groove 116 is aligned with and has substantially the same width as slot 114. Groove 116 slidably mates with the elongate rib 78 on the inner surface of insulator housing 42. The sliding interengagement of groove 116 with rib 78 prevents the tube housing from rotating relative to insulator housing 42 and also aligns aperture 110 with slot 56.

Referring now to FIG. 19, the axial bore of tube housing 106 is characterized by a first relatively large diameter section 122, a tapered section 124, a relatively small intermediate section 126 and an intermediate diameter size section 128. Axial bore section 126 is sized to make a close sliding fit with support 100. The intermediate size bore section 128 is sized so as to tightly accommodate the proximal (rear) end of tube 102. The latter is fixed to tube housing 106 by a press fit or by other suitable means, e.g., by a cement or by soldering, brazing or welding as is deemed practical according to the materials being joined.

Figure 11:
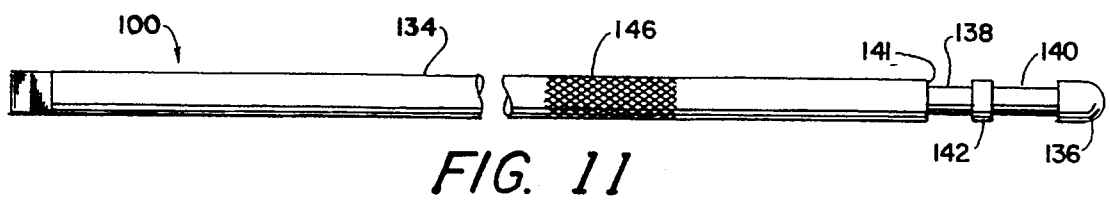
FIG. 11 is a plan view of a rod to which the tool head is connected.
Figure 12:
FIG. 12 is a side view showing the rod of FIG. 11 rotated 90° on its axis.
Figure 13:
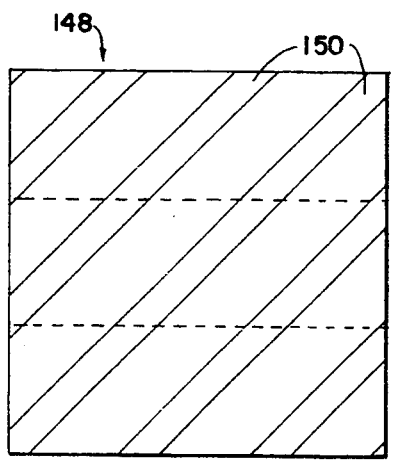
FIG. 13 is a side view of a helical gear that is affixed to the rod of FIG. 11.
Figure 14:
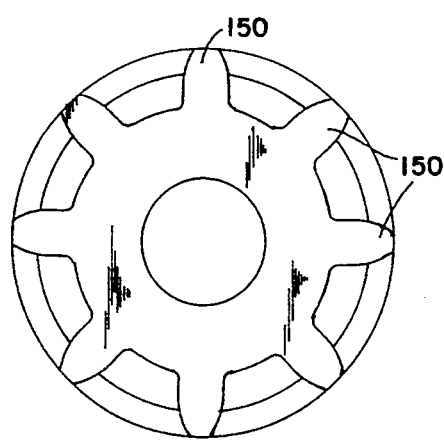
FIG. 14 is an end view of the gear of FIG. 13.
Figure 21:
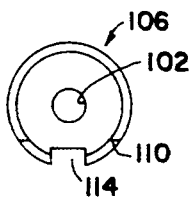
FIG. 21 is a front end view of the tube housing.
Figure 18:
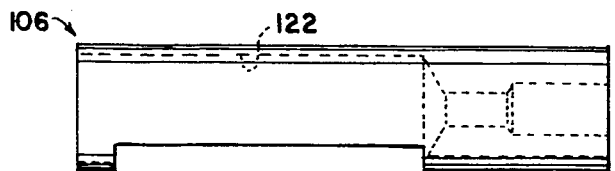
FIG. 18 is a side view in elevation of the tube housing.

Referring now to FIGS. 11 and 12, for the majority of its length, rod 100 has a constant relatively large size diameter as shown at 134. The proximal end of rod 100 is provided with a rounded head section 136 which is sized to make a close fit in the rounded rear end of the chamber formed by the mating cavities 28L and 28R. Intermediate sections 134 and 136 the rod has two reduced diameter sections 138 and 140 that are separated by an intermediate flange section 142 which preferably has a diameter close to that of rod section 134. An annular shoulder 141 is formed by the rod at its section 138. The opposite or distal end of rod 100 is formed so as to accommodate the tool head 6. Further details of the construction of the forward or distal end of support rod 100 are presented hereinafter.

The proximal (rear) end of rod 100 slidably extends through the bore section 126 of tube housing 106 and its intermediate or reduced diameter section 138 is accommodated by and makes a close fit in the circularly curved center hole 90 of cap 80. The radius of the hole 90 of cap 80 is smaller than the radius of the flange section 142 of the drive rod, while the length of rod section 138 is only slightly greater than the overall thickness of cap 80. As a result, shoulder 141 and flange 142 engage opposite sides of cap 80, thereby preventing rod 100 from moving axially relative to cap 80, and vice versa. Hence, if rod 100 is inserted into tube housing 106 and tube 102, and that resulting subassembly is then inserted into the insulator housing via its open end, and thereafter the reduced diameter plug section 92 of cap 80 is secured in the circularly curved section 44 of the insulator housing 42, rod 100 will be fixed relative to the insulator housing while tube housing 106 and tube 102 will be free to move axially relative to the rod and the insulator housing to the extent permitted by the difference in the length of tube housing 106 and the distance between end cap 80 and the junction of bore sections 60 and 62.

Figure 17:
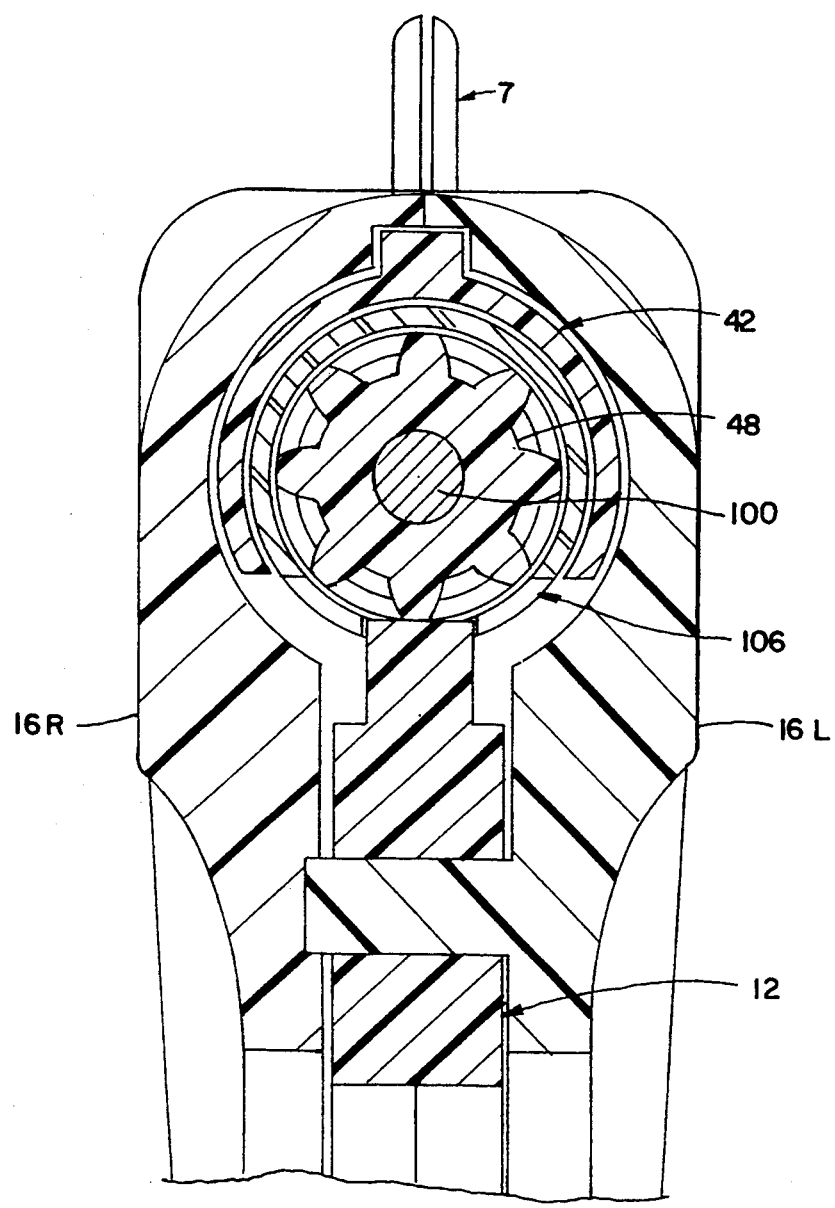
FIG. 17 is a cross-sectional view taken along line 17—17 of FIG. 1.
Figure 27:
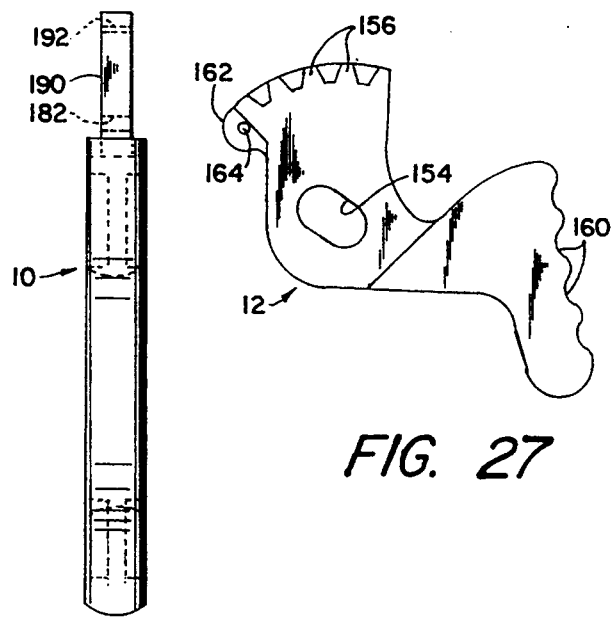
FIG. 27 is a side view in elevation of the rotational trigger member.

Looking now at FIGS. 10–14 and 17, rod 100 has a knurled section 146 which is slightly larger in diameter than its section 134 and is sized to accommodate a helical gear 148 having a center hole 149. The latter may be affixed to rod 100 by a press fit with knurled surface 146, or by means of a suitable cement or other fixing agent, e.g., an epoxy cement. Gear 148 may be made of a metal or a plastic. Rod 100 is preferably made of metal for electrical conduction purposes. The preferred mode of mounting helical gear 148 to the drive rod is by way of a friction fit, augmented by a suitable cement. Gear 148 has evenly shaped, helically-directed gear teeth 150. Gear 148 is sized so that a portion of its periphery projects through aperture 110 in tube housing 106 for engagement of its teeth 150 by the rotation trigger member 12 (FIGS. 10, 17 and 27).

Trigger member 12 has an elongate hole 154 for accommodating pivot pin 36A. Additionally, one end of that rotation trigger is provided with a plurality of helically pitched teeth 156 which are shaped and sized to mate with teeth 150 of gear 148. The opposite end of the trigger member is preferably knurled or formed with grooves 160 to eliminate slippage between the rotation trigger member and the surgeon's finger used to operate that trigger member. Trigger member 12 also has an extension 162 provided with a small aperture 164 which is sized to accommodate one end of a tension spring 166. The opposite end of the spring is formed with a circular extension sized to fit over pin 34A of the left handpiece 16L. Pivot hole 154 is elongated so as to facilitate operation of the rotation trigger. When the latter is mounted to pin 36A, spring 166 exerts a force that normally holds the rotation trigger in its forward and down position (FIG. 10), with its teeth 156 being out of engagement with gear 148. When that trigger is pulled back by a finger of the operating surgeon, its moves upwardly on pivot pin 36A and also rotates on that pin, causing its teeth 156 to engage and rotate helical gear 144, thereby causing rotation of drive rod 100. Rotation of trigger 12 is limited in one direction by its engagement with the surface 57 defining the forward end of slot 56 of the insulator housing 42, and in the other direction by its engagement with shoulders 170L and 170R (FIGS. 2 and 3) formed by handpieces 16L and 16R.

Referring now to FIGS. 10, 16, 25 and 26, trigger member 10 is preferably formed with an elongate aperture 180 to accommodate a finger of the surgeon. Additionally, the trigger member has a hole 182 to accommodate pivot pin 32A on the left handpiece. The trigger member has a reduced thickness end portion 190 that is provided with a rectangular notch 192 that subdivides its upper end into two fingers 193 and 195. The notch and fingers are sized so as to make a pivotal connection with lug 112 of tube housing 106. It is to be noted that handpieces 16L and 16R have recesses 17L and 17R to accommodate the reduced thickness end portion 190 of the trigger member. Trigger member 10 is pivotally mounted so that its notch 192 is engaged with lug 112.

Pivotal movement of trigger 10 causes axial movement of tube housing 106 and tube 104 when the trigger member is pivoted toward and away stationary handle 8. Pivotal movement of trigger 10 relative to the stationary handle 8 is illustrated by the arrows in FIG. 1. Pivotal movement of trigger 10 causes the tube housing to move in insulator housing 42 between a first rearward limit position (FIG. 1) wherein tube housing 106 is stopped by engagement with end cap 80 and a second forward limit position wherein the distal (forward) end of the tube housing is blocked by the tapered bore section 62 of the insulator housing.

Figures 15, 16:
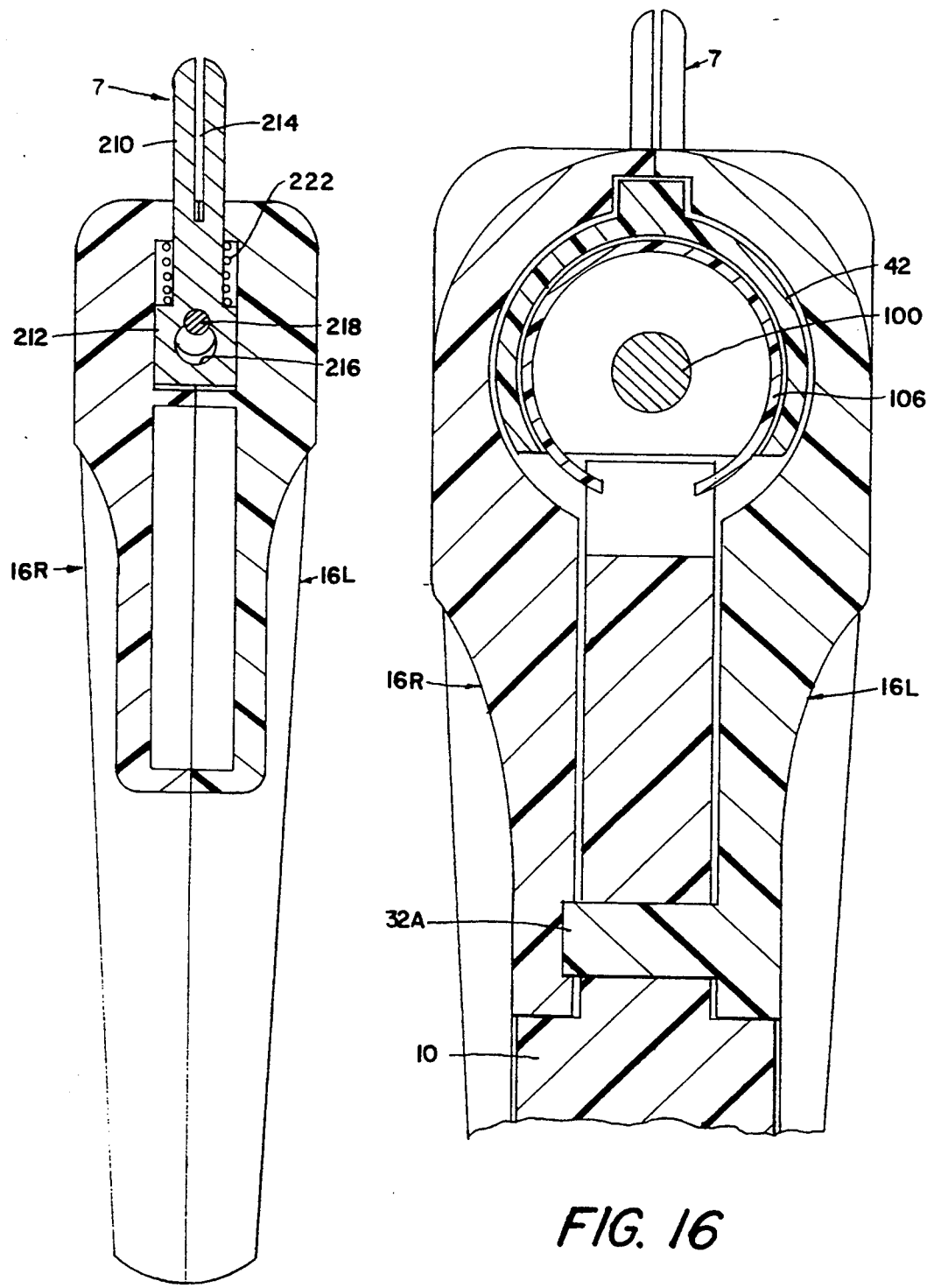
FIG. 15 is a cross-sectional view taken along line 15—15 of FIG. 1.
FIG. 16 is a cross-sectional view along line 16—16 of FIG. 1.

Referring now to FIGS. 10 and 15, the electrical terminal pin 7 is made of metal and comprises a round pin section 210 and an enlarged head section 212. Preferably pin section 210 is bifurcated as a result of a slot 214 so as to be compressible radially when coupled to a mating female connector. Head section 212 is generally round in cross-section except that it has diametrically opposed flat surfaces that mate with corresponding flat surface portions 25A and 25B (FIG. 2) of cavities 24L and 24R. Pin 7 also has a keyhole that extends perpendicular to its flat surfaces and comprises an enlarged section 216 and a reduced section 218. The latter section has a radius of curvature larger than that of section 140 but smaller than that of flange 142 and rounded end 136 of rod 100. The enlarged section 216 has a radius of curvature larger than the rounded end 136 of rod 100. A compression spring 222 surrounds pin section 210 in the hole formed by cavities 24L and 24R, being captivated between head section 212 and the shoulder formed by the intersection of cavities 26L and 26R with cavities 24L and 24R respectively. Spring 222 normally urges the terminal pin inwardly so as to have rod section 140 locked in keyhole section 218.

Referring now to FIGS. 13-15 and 22, tool head 6 can take various forms. In this preferred embodiment of the invention, it takes the form of a releasable scissors-type head.

Figure 22:
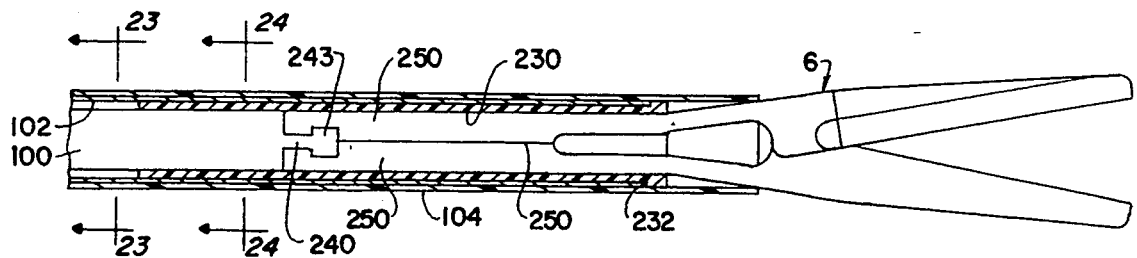
FIG. 22 is an enlarged cross-sectional view of a portion of the tool head drive assembly.
Figure 24:
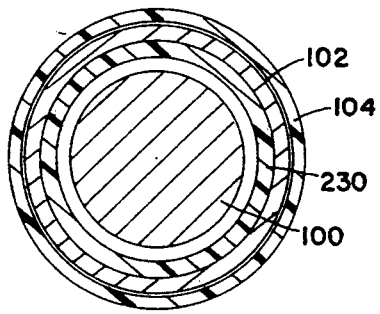
FIG. 24 is a cross-sectional view taken along line 24—24 of FIG. 22.
Figure 23:
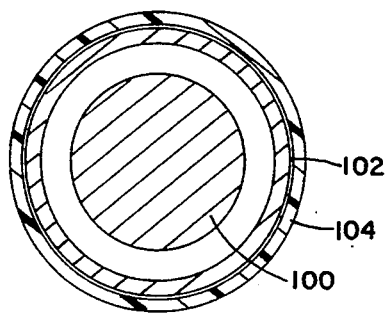
FIG. 23 is a cross-sectional view taken along line 23—23 of FIG. 22.
Figures 25, 26:
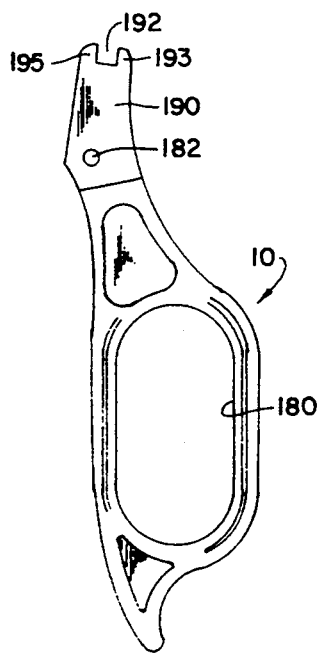
FIG. 25 is a side elevation of the operating trigger member.
FIG. 26 is a front end view in elevation of the trigger member of FIG. 25.

In this connection it should be noted that it is preferred to provide the outer tube or sleeve 102 with a tubular sleeve-type bearing 230 (FIGS. 22 and 24) having a peripheral flange 232. Bearing 230 fits inside of and is bonded to tube 102, with the distal end of the tube engaging peripheral flange 232 as shown in FIG. 22. Bearing 230 may be made of TEFLON or some other commercially available material that has a relatively low coefficient of friction and the hardness required to withstand wear from repeated sliding contact with the tool head. The i.d. of bearing 230 is slightly larger than the o.d. of rod 100 and the o.d. of the body sections 250 of scissors blade members 246A and 246B hereinafter described.

Referring now to FIGS. 1, 22-24 and 28-30, tool head 6 is detachably secured to rod 100 so as to be locked against rotational or axial movement relative to the rod. For this purpose, rod 100 is provided with a tongue 240 having an enlarged head 242, with both the tongue and head having a pair of flat opposite surfaces 241 and 243 respectively. Tool head 6 is preferably formed of two identical scissors blade members 246A and 246B formed of a stainless steel with spring-like quality. Each blade member comprises a body section 250 that is semi-circular in cross-section, so as to have a flat face 252. In addition, each body section is notched and its flat face 252 is recessed as shown at 260 and 262 so that when the two faces are brought into confronting relation with one another, a bayonet slot 264 is formed as shown in FIG. 28 that is sized to mate with tongue 240 of rod 100 as shown in FIG. 22.

Still referring to FIGS. 22-25, blade members 246A and 246B are formed with spring arms 268 that are integral with body sections 250 and carry integral scissors blades 270. Arms 268 are formed so that in their normal state the scissors blades extend at an inclined angle to the longitudinal axes of body sections 250 (FIG. 28). An edge portion of each scissors blade is ground so as to provide a micropolished flat scissors face as shown at 272 that terminates in a sharp edge 274. Each scissors blade 270 is formed so that it is bent longitudinally as viewed in FIG. 30, so that its forward end or tip crosses the center axis of its associated body section 250. Accordingly, when the two scissors blade members are secured together at their flat faces 252 (FIG. 28) by welding or other means, so as to form bayonet slot 264, the scissors faces 272 are engaged with one another at their proximal or rear ends (FIG. 30), while their forward ends are separated (spaced apart) from one another (FIG. 28) but extend laterally across the center axis of the tool head, i.e., across the planes of faces 252. Consequently, if a radially-directed squeezing force is applied to blades 270 normal to faces 252 (as represented by the mutually-converging arrows in FIG. 28), the blades will be forced together, and when that occurs, the resulting interference caused by the fact that the blades cross one another (as seen in FIG. 30) will cause the blades to deflect back away from one another to an extent just sufficient to permit the sharp edges 274 to close on one another in a scissors-like cutting action.

As seen in FIG. 22, the scissors head 6 is sized so that its body sections 250 can slide within bearing sleeve 230. Also, blades 270 are sized so that they also can fit within and slide relative to bearing 230 when they are fully closed on one another.

Assembly of the tool involves several separately conducted subassembly procedures. The tool head 6 is assembled by welding or brazing blade members 246A and 246B together. In a separate procedure, helical gear 148 is mounted onto and secured to rod 100. Then tool head 6 is attached to rod 100 by inserting the rod's tongue 240 into bayonet slot 264.

Contemporaneously, or before or after the foregoing steps, tube 102 is affixed to tube housing 106, and tubular sheath 104 is affixed to insulator housing 42. Thereafter, rod 100, with tool head 6 attached, is inserted into the proximal (rear) end of tube housing 106 and forced forwardly so as to cause the scissors blade arms 268 to yield enough to allow scissors blades 270 to close on one another enough to permit the tool head to pass through tube 102 and bearing 230, and also to locate gear 148 in bore section 122. The diameter of bore section 122 is slightly oversized with respect to helical gear 148 so as to permit the gear to rotate therein. Thereafter, or before insertion of rod 100 into the tube housing, end cap 80 is mounted onto rod 100 as previously described. In this connection, it is to be noted that the semi-circular hole 90 in cap 80 is slightly larger than the diameter of rod section 138, while preferably the width of slot 88 in cap 80 is slightly smaller than the diameter of rod section 138, with the result that the end cap makes a snap fit with the drive rod. Molded cap 80 has flexibility that permits it to yield enough to allow rod 100 to be forced through slot 88 into hole 90.

Thereafter, the subassembly consisting of tube 102, tube housing 106, rod 100 with gear 148, and tool head 6, is slipped into the proximal (rear) end of insulator housing 42, with the internal rib 78 of the insulator housing being aligned and disposed in groove 116 and slot 114 of the tube housing. This step involves inserting tube 102 into sheath 104 so that blades 270 can project from the forward (distal) end of the sheath. When the subassembly consisting of tube 102, tube housing 106, etc., is inserted into the insulator housing, it is preferred that rod 100 be withdrawn enough in tube housing 106 (as viewed in FIGS. 10 and 22) to permit sleeve bearing 230 to surround scissors blades 270 and thereby apply a radially directed compression force that holds the blades in closed position. Having the scissors blades closed by bearing 230 facilitates insertion of the blades and tube into sheath 104. Thereafter rod 100 is shifted axially so as to permit end cap 80 to be seated in the rear end of the insulator housing, and end cap 80 is secured to that housing by a suitable cement or by ultrasonic welding as previously described. The internal rib 78 in insulator housing 42 cooperates with groove 116 and slot 114 to insure that the aperture 110 of the tube housing is in confronting alignment with the trigger member 10 when subsequently the resulting assembly is mounted to the handle assembly.

The foregoing combined subassemblies consisting of insulator housing 42 and its attached sheath 104, and tube housing 106 and its associated parts, is then combined with the handle assembly. The latter may be pre-assembled by starting with left handpiece 16L and first mounting trigger member 10 on pivot pin 32A. Simultaneously, or before or after the foregoing step, the rotational trigger 12 is placed onto the post 36A with its teeth engaged with helical gear 148, and the spring 166 attached thereto is subsequently attached to the post 34A. Then terminal pin 7, with compression spring 222 mounted thereon, is placed into cavities 24L and 26L, with spring 222 being compressed so as to provide a force urging pin 7 inwardly (downwardly as viewed in FIG. 10). Then the right handpiece 16R is placed over the foregoing assembly into engagement with the left handpiece 16L and the two handpieces are secured together by a suitable cement or by ultrasonic welding.

The handle assembly is attached to the assembly consisting of insulator housing 42 and tube housing 106, etc. by the simple expendent of inserting the insulating housing into the front end of the chamber formed by cavities 20L and 20R. When this is done, the rounded rear end of rod 100 engages the small keyhole section 218 and coacts with the edge of that keyhole section to cam pin 7 outwardly enough to align the enlarged keyhole section 216 with the rod, thereby allowing rod section 140 to be forced into alignment with the pin, whereupon spring 222 will force the pin inwardly again to lock rod 100 to the terminal pin, in turn locking the insulator housing to the handle assembly.

It is to be noted that when inserting the insulator housing into the handle assembly, the trigger 10 must be pulled back to its rear limit position as shown in FIG. 10 so as to permit the insulator housing 42 and cap 80 to clear the finger section 193 of the trigger, but the finger section 195 projects up far enough to intercept the lug. Thereafter, assuming that the insulator housing has been locked to the handle assembly, reverse movement of the trigger back to the position of FIG. 1 will cause finger section 193 to engage the lug and thereby move the tube housing rearwardly in the insulator housing.

As mentioned hereinabove, the elongate pivot hole 154 of the rotational trigger is sized so that spring 166 will hold it in a down and forward position (FIG. 10), in which position its teeth 156 do not protrude into the insulator housing far enough to intercept gear 148 and thus interfere with its axial movement when the tool assembly comprising the insulator housing and tube housing 106 is inserted into or pulled out of the handle assembly. To further facilitate detachment of the tool assembly from the handle assembly, the slot 114 in tube housing 106 is sized so as to provide clearance with trigger teeth 156 as the housing is inserted into or removed from the handle housing 16L,16R.

Operation of the tool is as described hereinafter.

When trigger member 10 is in its forward limit position (FIG. 1), tube housing 106 and tube 102 are in their withdrawn or retracted position wherein bearing 230 terminates short of engagement with the blades 270 of tool head 6, with the result that the blades are in their separated or open position (FIGS. 1, 22 and 28). When trigger member 10 is pulled toward fixed handle 8 to its other limit position (FIG. 10), the pivotal connection between the trigger member and lug 112 of tube housing 106 causes the latter to be moved forward in housing 42, causing tube 102 to telescope forwardly and causing bearing member 230 to slip over and compress scissors blades 270 into closing position.

The angular orientation of scissors blades 230 relative to the handle assembly can be varied by manipulation of rotational trigger member 12. When trigger member 12 is pulled back, its gear teeth cause helical gear 148 to rotate, thereby rotating rod 100 and the tool head counterclockwise (as viewed in FIG. 17) relative to the fixed handle member 8. Because trigger member 12 has only a limited number of teeth, it must be retracted and then released several times in order to rotate the tool head 360°. By way of example but not limitation, the number of teeth on rotational trigger 12 and the number of teeth and the pitch thereof on helical gear 148 may be set so that trigger 12 must be pulled back and released approximately 8 times in order to achieve a 360° rotation of the tool head.

The preferred tool design described above offers a number of advantages. For one thing, the tool comprises several discrete lower tier subassemblies plus two discrete higher tier or major subassemblies, one of the major subassemblies being a multi-component handle assembly and the other comprising insulator housing 42, sheath 104, cap 80, tube housing 106, tube 102, rod 100, helical gear 148 and tool head 6, with the latter major subassembly being releasably secured to the handle assembly. Detachment of this higher tier or major subassembly from the handle assembly is achieved by pulling the terminal pin outwardly (upwardly as viewed in FIG. 10) so as to align the enlarged portion 216 of its keyhole with the rounded head 136 of rod 100, thereby allowing the handle assembly to be pulled free of rod 100. As a result, the major subassembly comprising insulator housing 42, sheath 104, cap 80, tube housing 106, tube 102, rod 100, helical gear 148 and tool head 6 can be replaced by a new and like substitute subassembly. In other words, the handle assembly is reusable with different substitute tool assemblies.

A second advantage resides in the fact that the scissors head shown in the drawings is removable from rod 100. A third advantage is that different tool heads may be used in place of the scissors head shown in the drawings. Thus, for example, the tool head may be a grasper head comprising a pair of jaws with confronting serrated surfaces that can be forced together by forward movement of tube 102 into grasping relation with tissue at a surgical site. The tool head also may comprise a combination grasper/cutter with one of the confronting faces of the two jaws having a cutting blade that is received in a notch in the other jaw. Another possibility is a tool head with cooperating members for holding a suture or a needle.

A fourth advantage resides in the fact that cap 80 need not be cemented to the insulator housing. Instead, as shown in dotted lines in FIG. 9, the cap could be provided with a peripheral groove 93 in its reduced section 92 and the insulator housing may be formed with an internal circumferentially-extending rib (not shown) sized to make a snap fit in groove 93, thereby permitting the cap to be releasably interlocked with the insulator housing. If such arrangement is adopted, the cap may be easily detached from the insulator housing out of connection with rod 100, thereby permitting the rod and its attached tool head to be withdrawn rearwardly out of tube 102 and insulator housing 42. This alternative embodiment facilitates removal and replacement of the subassembly consisting of rod 100, helical gear 148 and the tool head 6, or simply of replacement of the tool head 6.

A further advantage resides in the fact that the rotational trigger permits the surgeon to rotate the scissors blades relative to the handle assembly by a precise amount, thereby avoiding the need to rotate the handle assembly to achieve a particular cutting orientation of the scissors blades. The latter advantage is beneficial to the surgeon from the standpoint of comfort and ease of manipulation and ease of operation.

Still another advantage resides in the fact that bearing sleeve 230 applies a like force to each of the two scissors arms 268, with the force being distributed evenly about the circumference of the curved outer surfaces of scissors arms 268. Bearing 230 coacts with scissors arms 268 to urge blades toward one another as they are forced to close on one another.

A particularly significant advantage of this invention resides in the fact that rod 100 is stationary and surrounding tube 102 is reciprocated by manipulation of trigger member 10. This invention recognizes that surgeons need a point of reference in order to determine if and when they are moving a surgical scissors relative to the surgical site. In the absence of sheath 104, movement of outer tube 102 as seen by the surgeon might have a tendency to confuse the surgeon into believing that the tool is moving axially relative to the patient. The provision of outer sheath 104 eliminates the possibility of such confusion. Since sheath 104 is at least coextensive with tube 102 (and preferably projects slightly forward of tube 102 even when the tube is moved to its forwardmost position relative to rod 100) and hence conceals any axial movement of that tube relative to handle assembly 2, manipulation of handle members 8 and 10 causing the jaws to open and close is accomplished without the surgeon realizing that there is actual axial movement of tube 102. Instead, the surgeon sees that sheath 104 is stationary, with the result that the surgeon is free to concentrate his attention on the actual position of the scissors blades 230 (the latter do not appear to move toward and away from the patient when the jaws are opened or closed, unless the surgeon actually moves the tool relative to the patient).

Still another significant advantage is that the tool described above is adapted to conduct monopolar cauterization, but also may be used without being electrified. If the tool is to be made for non-cauterization uses, pin 7 need not be an electrically-conductive element and instead may function simply as a locking device for rod 100 as hereinabove described.

Other advantages will be obvious to persons skilled in the art.

MODIFICATIONS OF THE INVENTION

Persons skilled in the art will also appreciate that the invention is susceptible to various modifications. Thus, as noted above, various forms of tool heads may be used in practicing the invention. Also the tool head 6 may be permanently secured to the rod 100. Additionally, the manner of connecting various components may be varied. Thus, the proximal (rear) end of tube 102 may be externally threaded to mate with an internal thread formed in the bore section 128 of tube housing 106. Also, the insulator sheath 104 may be formed of a material which is sufficiently rigid to permit it to be formed with an external screw thread, thereby permitting it to mate with a cooperating internal thread formed in bore 66 of insulator housing 42. A further possible modification resides in the fact that a different tool head may be attached to the operating rod 100. For example, the tool head may comprise a grasper arrangement, e.g., a grasper arrangement as disclosed in U.S. Pat. No. 3,404,677, issued Oct. 8, 1968 to H. A. Springer for "Biopsy And Tissue Removing Device".

FIG. 31 shows another modification of the invention wherein a compression spring 290 is mounted on rod 100 between the forward end of tube housing 106 and the tapered bore section 162 of insulator housing 42. Spring 290 urges tube housing 106 rearwardly in the insulator housing so that it is intercepted by cap 80, in which position the tube housing holds trigger member 10 in its forward (open) position as shown in FIG. 1.

Still another possible modification is to provide a different form of pivotal connection between trigger 10 and tube housing 106. Thus, for example, tube housing 106 could be provided with a radially-extending external projection having a pivot hole, and trigger member 10 could be provided with a pivot hole designed to mate with the pivot hole on the external extension of the tube housing, with a separate pivot pin being inserted into the mating pivot holes and secured in place so as to pivotally connect the trigger to the extension on the tube housing.

Still another possible modification involves connection of the electrical terminal pin to drive rod 100. It is envisioned that the proximal (rear) end of rod 100 may be provided with a threaded axially-extending hole, and the terminal pin may be attached to rod 100 by providing the terminal pin with an externally-threaded front end that screws into the tapped hole in the end of the rod. In such event, the terminal pin may extend parallel rather than at a right angle to the longitudinal axis of the insulator housing. A further possibility is to use a separate electrically conductive screw to secure the conductive terminal pin to the threaded axially extending hole in the rear end of rod 100.

Another contemplated modification is to provide a scissors head wherein the two blade members 246A and 246B are not permanently secured together by welding or brazing but instead are releasably or permanently affixed in an adapter member (not shown) that is designed to mate with the forward end of rod 100. The adapter may be releasably or permanently cocupled to the rod.

Since still other changes may be made in the apparatus without departing from the scope of the invention herein involved, it is intended that all matter contained in the above description or shown in the drawings shall be interpreted in an illustrative and not in a limiting sense.

What is claimed is:

1. A surgical instrument comprising:
    a handle assembly, said handle assembly having a handle unit and a trigger member pivotally mounted to said handle unit, said trigger member being movable on its pivot between first and second positions;
    an elongate rod having a proximal end and a distal end;
    means mounted in said handle unit for releasably securing said proximal end of said rod to said handle unit so that said rod forms an extension thereof;
    a tool head attached to said distal end of said rod, said tool head comprising first and second cooperating tool members movable relative to one another between a first open position and a second closed position, said first and second tool members normally being in said first open position;
    a hollow tube coaxially and slidably surrounding said rod, said tube having a first proximal end slidably received in said handle unit and a second distal end that is movable into and out of overlapping relation with said first and second operating tool members as said hollow tube is reciprocated axially relative to said rod;
    force transmitting means connecting said hollow tube and said trigger member for causing said hollow tube to shift axially relative to said rod between (1) a first retracted position when said trigger member is in its said first position and (2) a second extended position when said trigger member is in its said second position, said first and second tool members being in said first open position and said distal end of said hollow tube being in a non-biasing position relative to said tool head when said hollow tube is in its first retracted position, said distal end of said hollow tube overlapping and biasing said said first and second tool members into said second closed position when said hollow tube is moved to its said second extended position, said force transmitting means comprising a coupling member attached to the proximal end of said hollow tube and surrounding said rod; and
    means attached to said handle unit for slidably supporting said coupling member for reciprocal movement relative to said rod lengthwise of the axis of said rod;
    said force transmitting means further comprising first and second mutually engaging means on said coupling member and said trigger member respectively that form a pivotal connection between said coupling member and said trigger member, whereby pivoting movement of said trigger member relative to said handle unit causes said hollow tube to shift axially relative to said rod from one to the other of said first retracted position and said second extended position.

2. A surgical instrument according to claim 1 wherein said means for securing said rod to said handle unit is mounted for movement between a first rod-locking position and a second rod-releasing position.

3. A surgical instrument according to claim 1 wherein said rod and said tool head are electrically conductive, and said means for securing said rod to said handle unit comprises an electrically conductive terminal member.

4. A surgical instrument according to claim 3 wherein said terminal member extends through a hole in said handle unit and comprises a first inner portion connected to said rod and a second outer portion projecting outside of said handle assembly.

5. A surgical instrument according to claim 4 further comprising spring means urging said terminal member into said first rod-locking position.

6. A surgical instrument according to claim 1 wherein said coupling member comprises a tube housing having a proximal end and a distal end with said proximal end of said hollow tube being fixed to the distal end of said tube housing, and further wherein said second means comprises a bifurcated end on said trigger member that makes a pivotal engagement with said first means on said tube housing, whereby said tube housing and said hollow tube are caused to move relative to said rod along the axis thereof when said trigger member is moved from one to the other of its said first and second positions.

7. A surgical instrument according to claim 6 wherein said handle unit comprises first and second opposite side members secured to one another, said first and second side members defining a chamber in which said tube housing is slidably disposed.

8. A surgical instrument according to claim 1 wherein said tool head is a scissors head, and said first and second tool members are scissors blades.

9. A surgical instrument according to claim 1 wherein said means for slidably supporting said coupling member is a hollow member that is mounted in said handle unit and has an elongate chamber in which said coupling member is slidably disposed for reciprocal movement relative to said handle unit lengthwise of the axis of said rod.

10. A surgical instrument according to claim 1 further including manually operable means for rotating said rod and said tool head relative to said handle unit, said manually operable means comprising a first gear means affixed to said rod, an auxiliary trigger member pivotally mounted to said handle unit, and a second gear means on said auxiliary trigger member cooperatively engaged with said first gear means, said second gear means being adapted to cause rotation of first gear means and thereby rotation of said rod when said auxiliary trigger means is pivoted relative to said handle unit.

11. A surgical instrument according to claim 1 comprising a second tube that is fixed to said handle assembly and surrounds and conceals movement of said first-mentioned tube.

12. An instrument according to claim 11 wherein said second tube does not overlap said tool head but has a length sufficient to conceal said first-mentioned movable tube as said first-mentioned tube is moved by manipulation of said trigger member.

13. A surgical instrument according to claim 1 further including tool rotating means for rotating said rod and tool head relative to said handle assembly and said first and second tubes.

14. A surgical instrument comprising:
    a handle assembly, said handle assembly including first and second manually graspable members pivotally mounted to one another so that said second member is movable on its pivot between first and second positions relative to said first member;

an elongate rod having a proximal end and a distal end with said proximal end secured to said first graspable member so that said rod forms an extension of said first manually graspable member;

a tool head attached to said distal end of said rod, said tool head comprising first and second cooperating tool members movable relative to one another between first and second tool member positions, said first and second tool members normally being in said first tool member position;

a hollow tube coaxially and slidably surrounding said rod, said tube having a first proximal end slidably received in said first manually graspable member and a second distal end that is disposed so as to be movable into overlapping relation with said tool head; and force transmitting means connecting said hollow tube and said second manually graspable member for causing said hollow tube to shift axially relative to said rod between (1) a first retracted position when said second manually graspable member is in its said first position and (2) a second extended position when said second manually graspable member is in its said second position, said first and second tool members being in said first tool member position and said distal end of said hollow tube being in a non-biasing position relative to said first and second tool members when said hollow tube is in its first retracted position, said distal end of said hollow tube being disposed to engage and bias said first and second tool members into said second tool member position when said hollow tube is moved to its said second extended position;

said force transmitting means comprising a hollow housing secured to said first proximal end of said tube and surrounding said rod, said hollow housing being disposed in a chamber in said first manually graspable member and movable in said chamber longitudinally lenthwise of the axis of said rod, and means pivotally connecting said hollow housing and said second manually graspable member for causing said hollow housing and said tube to shift axially as said second manually graspable member is pivoted relative to said first manually graspable member.

15. A surgical instrument comprising:
a handle assembly, a tool head, and drive means connecting said handle assembly and said tool head;
said handle assembly comprising a handle and a trigger member pivotally mounted to said handle;
said tool head comprising first and second cooperating tool members movable between a first open position wherein they are spaced from one another and a second closed position wherein they are proximate to or engaged with one another; and
said drive means comprising an elongate rod, a tube surrounding said rod means, for releasably securing one end of said rod to said handle assembly, means for securing said tool head to the opposite end of said rod, support means attached to said handle for slidably supporting said tube for sliding axial movement relative to said rod, said support means comprising (1) a first housing releasably secured to said handle assembly and defining an elongate chamber, and (2) a second housing slidably mounted in said elongate chamber, said tube being secured to and movable with said second housing relative to said first housing lengthwise of the axis of said tube, and said rod extending through said second housing, and means connecting said support means and said trigger member whereby manipulation of said trigger member will cause said second housing and said tube to move axially relative to said rod between a first position wherein one end of said tube is retracted from said tool head and said first and second tool members are in said first open position and a second position wherein said tube overlaps said tool head and forces said first and second tool members into said second closed position;

said tool head and said drive means forming a discrete subassembly that is removably secured to said handle assembly.

16. A surgical instrument according to claim 15 wherein said rod and said tool head are made of electrically conductive material and said second housing and said tube are made of non-electrically conductive material, further including a second tube surrounding and concealing movement of said first-mentioned tube, said second tube being secured to said first housing and being sized so as to permit relative axial movement of said first-mentioned tube.

17. A surgical instrument according to claim 15 wherein said handle comprises a hollow body portion and said first housing extends within said hollow body portion of said handle.

18. A surgical instrument comprising:
a handle assembly, said handle assembly having at least a first handle member and a trigger member pivotally mounted to said first handle member, said trigger member being movable on its pivot between first and second positions;
an elongate rod;
means for securing said rod to said handle assembly so that said rod forms an extension thereof;
a tool head attached to said rod, said tool head comprising first and second cooperating tool members movable relative to one another between a first open position and a second closed position, said first and second tool members normally being in said first open position;
a hollow tube coaxially and slidably surrounding said rod, said tube having a first proximal end slidably received in said handle assembly and a second distal end that extends to said tool head and is movable axially into and out of overlapping relation with said first and second operating tool members; and
force transmitting means connecting said hollow tube and said trigger member for causing said hollow tube to shift axially relative to said rod between (1) a first retracted position when said trigger member is in its said first position and (2) a second extended position when said trigger member is in its said second position, said first and second tool members being in said first open position and said distal end of said hollow tube being in a non-biasing position relative to said tool head when said hollow tube is in its first retracted position, said distal end of said hollow tube being disposed to move said first and second tool members into said second closed position when said hollow tube is moved to its said second extended position;

said means for securing said rod to said handle assembly comprising a conductive terminal member having a key-shaped aperture characterized by a first relatively small diameter portion and a second relatively large diameter portion communicating with said first relatively small diameter portion, and the proximal end of said rod having (a) a relatively large diameter head section sized to fit in said relatively large diameter portion of said aperture but oversized with respect to said relatively small diameter portion of said aperture, and (b) a circumferential groove having a diameter smaller than said relatively small diameter portion of said aperture, said terminal member and said rod being positioned in said handle assembly so that said groove is positioned in alignment with said small diameter portion of said aperture, whereby said head section of said rod is captivated against axial movement relative to said handle assembly.

19. A surgical instrument comprising:
a handle assembly, said handle assembly having at least a first handle member and a trigger member pivotally mounted to said first handle member, said trigger member being movable on its pivot between first and second positions;
an elongate rod;
means for securing said rod to said handle assembly so that said rod forms an extension thereof;
a tool head attached to said rod, said tool head comprising first and second cooperating tool members movable relative to one another between a first open position and a second closed position, said first and second tool members normally being in said first open position;
a hollow tube coaxially and slidably surrounding said rod, said tube having a first proximal end slidably received in said handle assembly and a second distal end that extends to said tool head and is movable axially into and out of overlapping relation with said first and second operating tool members; and
force transmitting means connecting said hollow tube and said trigger member for causing said hollow tube to shift axially relative to said rod between (1) a first retracted position when said trigger member is in its said first position and (2) a second extended position when said trigger member is in its said second position, said first and second tool members being in said first open position and said distal end of said hollow tube being in a non-biasing position relative to said tool head when said hollow tube is in its first retracted position, said distal end of said hollow tube being disposed to move said first and second tool members into said second closed position when said hollow tube is moved to its said second extended position;
said tool head being removably attached to said rod by a tongue and groove connection.

20. A surgical instrument according to claim 19 wherein said tongue and groove connection is surrounded by said hollow tube when said hollow tube is in its first retracted position.

21. A surgical instrument comprising a handle assembly, a tool head, drive means connecting said handle assembly and said tool head, and tool head rotation means for rotating said tool head relative to said handle assembly;
said handle assembly comprising a handle and a trigger member pivotally mounted to said handle;
said tool head comprising first and second cooperating tool members movable between a first open position wherein they are spaced from one another and a s second closed position wherein they are proximate to or engaged with one another;
said drive means comprising an elongate rod, a hollow tube surrounding said rod, means for releasably securing one end of said rod to said handle assembly, means for securing said tool head to the opposite end of said rod, housing means for slidably supporting said tube for sliding axial movement relative to said rod, and means connecting said housing means and said trigger member whereby manipulation of said trigger member will cause said tube to move axially relative to said rod between a first position wherein said tube is retracted from said tool head and said first and second tool members are in said first open position and a second position wherein said tube is engaged with said first and second tool members and holds them in said second closed position;
said tool head and said drive means forming a discrete subassembly that is removably secured to said handle assembly; and
said tool head rotating means comprising a second trigger member pivotally attached to said handle assembly, and means coupling said rod and second trigger member for causing rotation of said rod and tool head when said second trigger member is moved about its pivot.

22. A surgical instrument comprising a handle and trigger assembly and an operating tool assembly separably connected to said handle and trigger assembly;
said handle and trigger assembly comprising a handle housing having a chamber therein and a trigger member pivotally mounted to said handle housing;
said operating tool assembly comprising at one end thereof a tool head with tissue-engaging members and at the opposite end thereof a tubular housing that extends into said chamber and is releasably connected to said handle housing, said tissue-engaging members being movable relative to one another between a first open position and a second closed position, said operating tool assembly further including a mechanism for moving said tissue-engaging members toward and away from one another, said mechanism including movable means in said tubular housing engaged and movable by said trigger member for causing said mechanism to move said tissue-engaging members toward and away from one another in response to pivotal movement of said trigger member;
said handle and trigger assembly further comprising locking means engaged with said operating tool assembly for releasably locking said tubular housing to said handle housing,
said operating tool assembly further comprising a rod having a proximal end and a distal end with said proximal end extending through said tubular housing and said distal end connected to and supporting said tool head, a hollow housing slidably surrounding said rod, said hollow housing being slidably disposed within said tubular housing, a hollow shaft disposed in coaxial and telescoping relation with said rod, said shaft having a proximal end affixed to said hollow housing and a distal end that is adapted to embrace said tissue-engaging members and force them into said closed position when said shaft is moved axially in a direction away from the proximal end of said rod toward the distal end of said rod, means locking said rod to said tubular housing, and means on said hollow housing for making a pivotal connection with said trigger member, whereby pivotal movement of said trigger member relative to said handle housing will cause said hollow housing and said shaft to shift axially according to the direction of pivotal movement of said trigger member;

said operating tool assembly further including a helical gear affixed to said rod; and said handle and trigger assembly further including an auxiliary trigger means pivotally mounted to said handle housing having gear teeth engaged with said helical gear so that pivotal movement of said auxiliary trigger means will cause rotation of said rod and said tool head.

23. A surgical instrument according to claim 22 wherein said tool head is a scissors head and said first and second tissue-engaging members comprise scissors blades attached to spring arms that are shaped to bias said blades to open position.

24. A surgical instrument comprising:
a handle unit having means defining an elongate chamber open at one end of said unit;
a trigger member pivotally mounted to said handle unit, said trigger member being movable on its pivot between first and second positions;
a hollow housing disposed in said elongate chamber and secured to said handle unit, said first hollow housing having a proximal end and a distal end, with said distal end thereof having an opening;
a hollow tube having a proximal end and a distal end, said proximal end of said hollow tube extending slidably through said opening in said first hollow housing;
a slide member slidably positioned in said elongate chamber, said slide member having a proximal end and a distal end;
said proximal end of said hollow tube being attached to said slide member so as to project from said distal end thereof;
an elongate rod having a proximal end and a distal end, said rod being disposed in said hollow tube and extending through said slide member, and said hollow tube being slidable axially relative to said rod;
means for locking said rod against axial movement relative to said handle unit so that said rod forms an extension of said handle unit;
a tool head attached to said distal end of said rod, said tool head comprising first and second cooperating spring biased tool members movable relative to one another between a first open position and a second closed position, said first and second tool members being spring biased to favor said first open position;
said hollow tube having a length such that its distal end is movable into and out of overlapping relation with said first and second operating tool members as said hollow tube is reciprocated axially relative to said rod; and
force transmitting means connecting said slide member and said trigger member for causing said slide member and said hollow tube to shift axially relative to said rod between (1) a first retracted position when said trigger member is in its said first position and (2) a second extended position when said trigger member is in its said second position, said first and second tool members being in said first open position and said distal end of said hollow tube being in a non-biasing position relative to said tool head when said hollow tube is in its first retracted position, and said distal end of said hollow tube overlapping and biasing said said first and second tool members into said second closed position when said hollow tube is moved to its said second extended position.

25. An instrument according to claim 24 wherein said elongate chamber has an end wall at its proximal end, and further wherein said rod is locked to said end wall.

26. An instrument according to claim 24 wherein said hollow housing is releasably secured to said handle unit.

27. An instrument according to claim 26 wherein said hollow housing is releasably secured to said handle unit by virtue of being interlocked with said rod adjacent the proximal end of said rod.

28. An instrument according to claim 27 wherein said hollow housing has an end wall at its proximal end and said end wall has a slot therein, and further wherein said rod extends through said slot and has a peripheral groove that is interlocked with said end wall.

29. An instrument according to claim 24 wherein said hollow housing has an end wall at its proximal end and the proximal end of said rod projects through said end wall, and further wherein said means for locking said rod against axial movement relative to said handle unit comprises a locking member that is mounted in a passageway in said handle unit so as to be movable between a first rod-locking position and a second rod-releasing position, said locking member having a first portion that is accessible on the exterior side of said handle unit and a second portion located within said handle unit that is adapted to interlock with said rod in said first rod-locking position and release said rod in said second rod-releasing position, and a spring means mounted within said handle unit that urges said locking member to remain in said first position.

30. An instrument according to claim 29 wherein said second portion of said locking member has a keyhole through which said rod extends, said keyhole having a first section that is oversized with respect to said rod and a second section that is sized and shaped to interlock with said rod, said spring means being adapted to urge said locking member in a direction to cause said second section to engage said rod.

31. An instrument according to claim 29 wherein said locking member is made of an electrically conductive material and said first portion is shaped to function as an electrical terminal post.

32. An instrument according to claim 24 wherein said handle unit and said trigger member form a first subassembly, said second housing and said tube comprise a second subassembly that is releasably connected to said first subassembly and separable as a unit from said first subassembly.

33. An instrument according to claim 24 wherein said handle unit comprises a handle portion and a body portion integral with one end of said handle portion, said elongate chamber being formed in said body portion and said open end of said chamber being remote from said handle portion, and said trigger member being pivotally mounted to said body portion and extending into said chamber.

34. An instrument according to claim 24 wherein said hollow housing has an axially-extending slot confronting said trigger member, and said trigger member has means forming part of said force transmitting means that extends into and is slidable along said slot and makes a pivotal connection with said slide member.

35. An instrument according to claim 24 wherein said hollow housing has a slot confronting said trigger member and said slide member has a lug portion, and further wherein said trigger member has a finger portion that extends into and is slidable along said slot and is pivotally engaged with said lug portion, whereby pivoting movement of said trigger member relative to said handle unit causes said hollow tube to shift axially relative to said rod.

36. An instrument according to claim 24 wherein said tool head is a scissors head, with said first and second tool members comprising scissors blades attached to spring arms that are secured to said rod and are shaped so as to bias said scissors blades into said first open position, said scissors blades extending across each other when in said first open position.

37. An instrument according to claim 24 wherein said tool head is releasably connected to said distal end of said rod by a tongue-and-groove connection.

38. An instrument according to claim 24 wherein said slide member has an elongate gear-receiving chamber and a slot communicating with said chamber, and further including a helical gear on said rod within said gear-receiving chamber, and manually operated gear means movably mounted to said handle unit and engaged with said helical gear for rotating said rod on its axis whereby to change the relative angular orientation of said tool head relative to said handle unit.

39. An instrument according to claim 24 further including spring means in said hollow housing in engagement with said slide member for urging said slide member to move said hollow tube out of overlapping relation with said tool members.

40. A surgical instrument comprising:
a handle assembly having first and second handle members movably connected for movement relative to one another;
an elongate rod having a distal end and a proximal end, said rod being releasably secured at its proximal end to said first handle member so as to form a fixed extension thereof;
a tool head coupled to the distal end of said rod, said tool head having first and second members movable toward and away from one another;
a hollow shaft coaxially and slidably surrounding said rod, said hollow shaft having a first end slidably received in said first handle member and a second end in position to be moved into and out of overlapping relation with said first and second members of said tool head;
drive means connecting said hollow shaft and said second handle member for causing said hollow shaft to shift axially relative to said rod between (1) a first retracted position when said second handle member is moved to a first position relative to said first handle member and (2) a second extended position when said second handle member is moved to a second position relative to said first handle member, said first and second tool head members being in a first open position relative to one another when said second handle member is in its said second position and being forced by said hollow shaft to close relative to one another when said second handle member is moved to its said first position, said drive means including a drive member that is attached to said first end of said hollow shaft and is slidably disposed in a chamber in said first handle member, and means coupling said second handle member to said drive member for causing said hollow shaft to shift axially relative to said rod in response to movement of said second handle member relative to said first handle member; and
manually operable means carried by said first handle member for rotating said rod relative to said first handle member, said hollow shaft and said tool head, said manually operable means being operable independently of movement of said second handle member relative to said first handle member;
said rod, said tool head and said hollow shaft comprising part of a discrete subassembly that is detachable as a unit from said handle assembly.

41. An instrument according to claim 40 wherein said rod is releasably secured to said first handle member by means comprising an electrically conductive terminal member mounted in said first handle member and interlocked with said rod so as to prevent removal of said rod from said first handle member, and further wherein said hollow shaft is made of an electrically insulating material and said rod and said tool head are made of electrically conductive material, so that said tool head may be used for cauterization purposes when said terminal member is connected to a source of electrical potential and said hollow shaft insulates said rod from direct contact with a patient engaged by said tool head.

42. An instrument according to claim 40 further including spring means mounted within said first handle member for urging said hollow shaft into said first retracted position whereby to allow said tool head to assume its open position.

43. A surgical instrument comprising:
a handle assembly having first and second handle members movably connected for movement relative to one another;
an elongate rod having a distal end and a proximal end, said rod being releasably secured at its proximal end to said first handle member so as to form a fixed extension thereof;
a tool head coupled to the distal end of said rod, said tool head having first and second members movable toward and away from one another;
a hollow shaft coaxially and slidably surrounding said rod, said hollow shaft having a first end slidably received in said first handle member and a second end in position to be moved into and out of overlapping relation with said first and second members of said tool head;
drive means connecting said hollow shaft and said second handle member for causing said hollow shaft to shift axially relative to said rod between (1) a first retracted position when said second handle member is moved to a first position relative to said first handle member and (2) a second extended position when said second handle member is moved to a second position relative to said first handle member, said first and second tool head members being in a first open position relative to one another when said second handle member is in its said second position and being forced by said hollow shaft to close relative to one another when said second handle member is moved to its said first position; and manually operable means carried by said first handle member for rotating said rod relative to said first handle member, said hollow shaft and said tool head, said manually operable means being operable independently of movement of said second handle member relative to said first handle member;

said means for rotating said rod comprising a movable trigger member mounted to said first handle member, a plurality of gear teeth carried by and movable with said trigger member, and a helical gear coaxially mounted on said rod, said helical gear being engaged by said gear teeth so that movement of said trigger member relative to said first handle member will cause rotation of said rod relative to said first handle member.

* * * * *

UNITED STATES PATENT AND TRADEMARK OFFICE
CERTIFICATE OF CORRECTION

PATENT NO. : 5,334,198
DATED : August 2, 1994
INVENTOR(S) : Rickey D. Hart et al.

It is certified that error appears in the above-indentified patent and that said Letters Patent is hereby corrected as shown below:

Claim 1, column 15, line 19, "saidrod" should be changed to -- said rod --;

Claim 1, column 15, line 43, delete "said" (second occurrence);

Claim 15, column 17, line 59, insert a "," after -- rod --;

Claim 15, column 17, line 59, delete the "," after -- means --;

Claim 21, column 20, line 4, delete the letter "s" before the word -- second --;

Claim 24, column 22, line 7, delete "said" (second occurrence).

Signed and Sealed this

Eleventh Day of October, 1994

Attest:

BRUCE LEHMAN

*Attesting Officer*  *Commissioner of Patents and Trademarks*